United States Patent [19]

Sultan et al.

[11] Patent Number: 4,982,615
[45] Date of Patent: Jan. 8, 1991

[54] STERILE CONTAINER FOR COLLECTING BIOLOGICAL SAMPLES FOR PURPOSES OF ANALYSIS

[76] Inventors: Bernard Sultan, 1 à 3 rue Solférino, Colombes (Hauts de Seine); Pierre Muraz, 321 avenue d'Argenteuil, Bois Colombes (Hauts de Seine), both of France

[21] Appl. No.: 339,652

[22] Filed: Apr. 18, 1989

[30] Foreign Application Priority Data

Apr. 18, 1988 [FR] France ............................. 88 05100

[51] Int. Cl.⁵ ............................................... G01N 1/12
[52] U.S. Cl. ............................. 73/864.51; 73/864.91
[58] Field of Search ........... 73/863.41, 863.51, 863.52, 73/864.51, 864.63, 864.91; 435/30, 292–295; 220/15, 94 R, 288, 85 CH, DIG. 14, 306; 128/760, 761; 604/317; 206/524

[56] References Cited

U.S. PATENT DOCUMENTS

| 602,324 | 4/1898 | Hautsch | 220/94 R |
|---|---|---|---|
| 3,777,739 | 12/1973 | Raitto | 128/760 |
| 3,900,019 | 8/1975 | Logiadis | 128/761 |
| 4,046,138 | 9/1977 | Libman et al. | 73/864.91 |
| 4,296,871 | 10/1981 | Andersson | 220/306 |
| 4,336,880 | 6/1982 | Mehl | 206/524.4 |
| 4,453,647 | 6/1984 | Neat | 220/288 |
| 4,494,581 | 1/1985 | Gordon | 73/863.41 |
| 4,643,326 | 2/1987 | Klingler | 220/94 R |

FOREIGN PATENT DOCUMENTS

| 0003577 | of 1910 | United Kingdom | 73/864.51 |
| 0444421 | 3/1936 | United Kingdom | 220/94 R |

*Primary Examiner*—Robert Raevis
*Attorney, Agent, or Firm*—Hughes & Multer

[57] ABSTRACT

A device intended to facilitate the taking of excretal biological specimens while eliminating the risk of contamination of the collected biological sample. The collected biological sample may be a urine sample or a stool sample. The device is characterized in that it comprises a flask with an open top end sealingly capped by a first cap, and a closed bottom capped by a second cap, the second cap being intended to seal the open top end after removal of the first cap and after introduction of the biological sample into the flask. An outer collar about the flask excludes contamination from the bottom cap during collection of the sample. The flask has an attachable handle. The handle has a flat tongue provided with a wide, longitudinally extending aperture for preventing drops of the sample from reaching the fingers of a person holding the flask.

14 Claims, 1 Drawing Sheet

STERILE CONTAINER FOR COLLECTING BIOLOGICAL SAMPLES FOR PURPOSES OF ANALYSIS

BACKGROUND OF THE INVENTION

The object of the present invention is a sterile container which facilitates the collection of an essentially urinary biological sample while considerably restricting contamination of the sample by possible outside germs, referred to as "contamination".

At the present time, the urinary sepcimen for cytobacteriological examination is in 95% of cases taken in the patient's home, the patient actually collecting the specimen of urine in a simple flask provided with a screwed stopper, which is then taken to the laboratory for analysis.

The disadvantages of using such a vessel are manifold:

At the level of the technique of taking the sample, the hand holding the flask will almost always be contaminated by the stream of urine because the sample has to be taken from the middle of the urination.

At the level of the cytobacteriological study, the interpretation of results will very often be falsified by indirect contamination of the urine specimen, of which the isolated or associated causes are essentially:

The sterile inside faces of the stopper but also and above all the exposed edge of the flask opening are brushed or touched by the fingers.

While the bottle is being filled, the cork may be provisionally set down on any non-sterile surface.

Accidental and frequent dropping of the stopper.

Prolonged exposure of its sterile inner faces to the non-sterile free air throughout the period of urination and even longer if the stopper is temporarily mislaid, which is far from being a rare occurrence.

SUMMARY OF THE INVENTION

The object of the present invention is to remedy these disadvantages and sets out to provide a means whereby it is possible to improve the technique of taking the specimen, ensuring the quality of the biological sample to allow better interpretation of the results of the biological analysis.

To this end, the invention relates to a device of the type mentioned hereinabove characterised in that it consists of a flask with an open top end capped by a first closure means having a closed end, capped by a second closure means, the second closure means being intended to cover the open top end after removal of the first closure means and introduction of the biological sample into the container.

Therefore, by reason of this device, the user first removes the means of occluding the opening in order to introduce the specimen and then he closes the opening again, using the second closure means which remains as a kind of reserve at the other end of the device. Thus, the device can be closed by a sterile occluding means, the sterility of the inside surfaces of the occluding means, at the level of the opening, have been ensured by the first closure means.

Therefore, this invention will find an application in medical biology: coproculture but above all cytobacteriological examination of urine, and it is this latter aspect which will be mainly developed here.

According to another characteristic feature, the first closure means is an operculum and/or a cap while the second closure means is a cap.

When the first closure means is an operculum, in other words a lid or cover, this may be protected from the bacteriological and mechanical points of view by a supplementary cap.

According to another characteristic feature, the top end and the bottom end are provided with an identical screwthread and the top and bottom caps are provided with a corresponding screwthread so that one can be screwed on the screwthread at the top end and the other on the screwthread at the bottom end, in a standby position and then on the screwthread at the top end after removal of the first cap and introduction of the biological sample.

Although the cap may be simply fitted onto the flask, it is worthwhile screwing it as in the embodiment in accordance with the characteristic features indicated hereinabove.

In order more satisfactorily to preserve sterility of the inner faces of this supplementary stopper, the wall of the flask comprises over its entire perimeter an outside reinforcing means which projects beyond the bottom screwthread, so constituting a small collar which is itself recessed on its bottom surface with a channel adapted to receive the free edge of the stopper over its entire circumference.

Still with a view to preserving the sterility of this "bottom" stopper, the wall of the flask is extended downwardly and by a few millimetres beyond the circular bottom of the container.

According to another characteristic feature, the flask is cylindrical and has a circular cross-section.

To facilitate gripping, it is a good idea for the flask to be provided with a handle and for this to have a wide opening in its centre.

The handle can be fixed rigidly to the flask or may be removable by means of a hook and aperture fitting.

According to another charactistic feature, the wall of the flask is extended downwardly beyond the bottom and constitutes a free circular edge on a bottom cylindrical closed end member and the bottom of the flask is lined with a bacteriostatic agent.

Thus, by way of example, the flask comprises on its wall, at about two-thirds of its height, a right-angled hook which is open at the bottom so that it can receive a flat handle provided with a transverse slot at its proximal end and on the flat surface, the handle being provided with a wide longitudinally extending aperture to avoid possible drops of urine reaching the fingers of the person holding the flask.

Thus, the advantage of this invention resides in having available a sterile flask:

the opening of which is initially and provisionally hermetically sealed by a sterile occluding means which will no longer be used for re-closing the filled flask, because this would be highly likely to have been contaminated while the specimen was being taken. After the flask has been opened, therefore, this occluding means will be disposable:

the final closure of which after filling will be performed by means of another sterile occluding means which is quickly freed from the bottom part to which it was hitherto attached, and where it will not have been subject to any risk of contamination.

The whole assembly is provided with a handle which makes it possible to keep the hand holding the flask well away from the sterile exposed edges thereof.

Thus, when the urine specimen is being taken, the patient holds the flask by the end of its handle, opens it and throws away the stopper which initially closed the flask, takes the sample of urine, once the flask is filled, rapidly removes the other sterile stopper from the bottom so that he can immediately and without releasing it use this in order finally to close the flask.

All the risks of contaminating the urine specimen which were listed earlier have thus been avoided.

In order to take samples of stool, the same method will be used with, above all, a wider flask and a strong and longer rigid handle.

BRIEF DESCRIPTION OF THE DRAWINGS

A simple and preferred embodiment of the invention is described hereinafter, reference being made to the accompanying drawings in which.

DETAILED DESCRIPTION OF THE INVENTION

Figure 1:
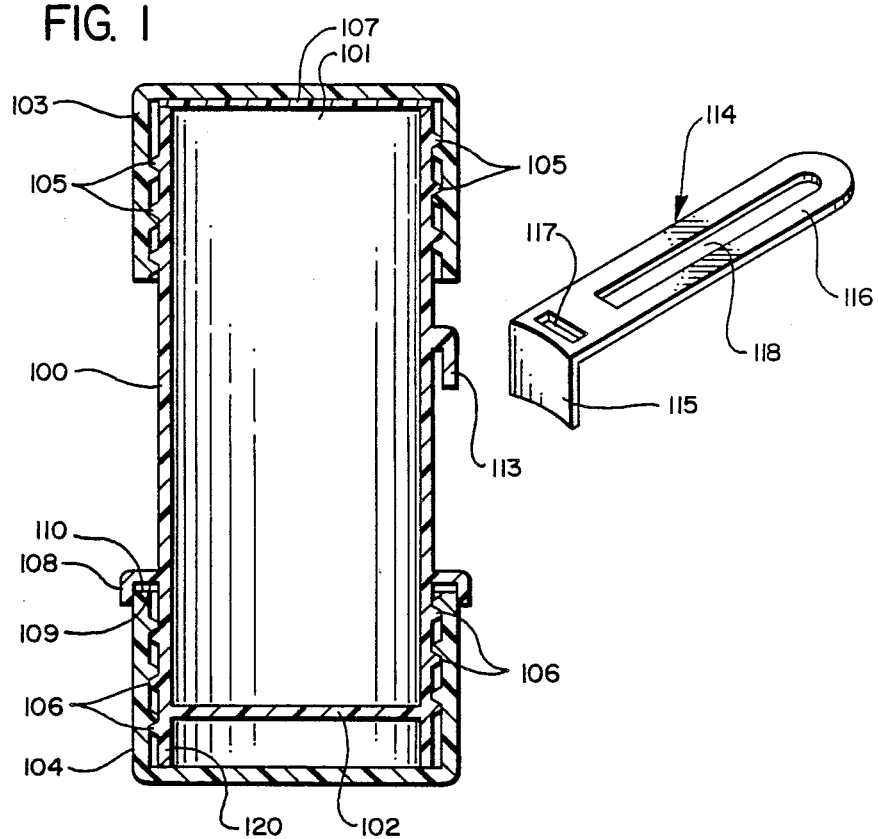
FIG. 1 shows the device according to the invention in longitudinal section and shows the handle in a perspective view.

According to the embodiment shown in FIG. 1, the invention refers to a device intended to facilitate the taking of a urine specimen while eliminating the risks of the biological sample which is thus collected being contaminated. This device consists of a flask 100 having an open top end 101 and a closed bottom 102. The open top end 101 is capped by a first occluding means 103 in the form of a cap, while the bottom end 102 is capped by a second occluding means 104 which is in a protected and standby situation. According to the example shown in FIG. 1, the two caps 103, 104 are provided on the inside with a screwthread, not shown, adapted to co-operate with the screwthread 105 on the top end and the screwthread 106 on the bottom end.

According to an alternative embodiment, the top end is closed by a detachable operculum 107 which may or may not be covered by a cap 103. In this case, this operculum (with or without the cap 103) constitutes the first occluding means.

In FIG. 1, the bottom end is extended beyond the bottom 102 by a circular free edge 120 forming a bottom closure member intended to complete the sealing-tightness and ensure perfect sterility of the stopper.

For use, the first occluding means, that is to say the cap 103 and/or the operculum 107, is removed so that the specimen can be taken and then the cap 104 is used, having been hitherto in a protected situation, in order to close the flask again.

According to the invention, the flask 100 may be of any shape; generally, it will be a cylindrical flask of circular cross-section. This flask may consist of any rigid plastics material which is more or less flexible and which has the capacity of about 40 ml.

According to FIG. 1, the cap 104 fits under an outer reinforcement 108 which constitutes a collar and of which the bottom surface is provided with a recessed groove 109 which receives and protects the top edge 110 of the cap 104.

According to the invention, in the event of the caps 103 and 104 being fixed by being screwed, their screwthreads are the same and the screwthreads 105 and 106 are likewise identical.

To distinguish between the caps or more generally the occluding means 103 and 104, these are of different colours.

According to an alternative embodiment, not shown, the membrane or operculum 107 which closes the top opening 101 of the flask 100 is not covered by a cap; this operculum is simply fixed by being glued or in some other manner to the free edge of the opening 101.

According to another alternative embodiment, not shown, the occluding means or caps 103, 104 are simply engaged by friction on the corresponding end of the flask or are clipped into position.

Figure 2:
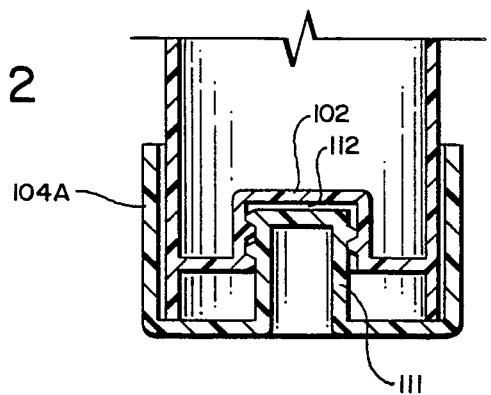
FIG. 2 is a sectional view of an alternative form of bottom end of the device according to an alternative embodiment.

FIG. 2 shows another alternative method of fixing the bottom cap 104A which comprises a screwthreaded central boss 111 which is screwed into the cavity 112 in the bottom 102 of the flask which is partially illustrated.

According to the invention, the flask 100 is provided with a handle or grip which may be fixed, removable or capable of being folded over. In the embodiment shown in FIG. 1, the handle is adaptable and for this purpose the flask 100 comprises a downwardly curved hook 113 and the adaptable handle 114 comprises a front loop 115 shaped like a segment of a circular cylinder or more generally shaped to match the shape of the wall of the flask 100 and is extended by a tongue 116 provided at the front with a slot 117 adapted to receive the hook 113 and at the rear with a large and elongated aperture or slot 118 extending over the entire length of the handle member 116.

This handle may likewise be capable of being folded over, for example by means of a hinge.

According to other alternative embodiments, not shown, the bottom cap may be fixed by a paper collar or other adhesive means set across the edge of the cap and the collar 107.

According to another alternative embodiment, there is likewise a top collar, not shown, in which fits the bottom edge of the top cap 103, still with a view to ensuring a safeguard against contamination.

Finally, it may be worth while introducing a bacteriostatic agent into the flask to prevent propagation of germs in the event of contamination.

What is claimed is:

1. A device intended to facilitate the taking of an excretal biological sample while eliminating the risks of contamination of the biological sample which is thus collected, the device being characterized in that it comprises a flask (100) having an open top end (101) sealingly capped by a first closure means (103, 107), a closed bottom end (102) capped by a bottom cap (104), and an outer collar (108) mounted about the flask (100) and incorporating a recessed groove (109) at the bottom side of the collar (108) to cover the edge (110) of the bottom cap (104) so as to exclude contamination from the bottom cap (104) when this latter is capping the bottom end (102) of the flask (100), the bottom cap (104) being intended to fit over the open top end (101) after removal of the first closure means (103, 107) and introduction of the biological sample into the flask (100).

2. A device according to claim 1, characterized in that the first closure means is a top cap (103).

3. A device according to claim 2, characterized in that the top end and bottom end are provided with identical screwthreads (105,106), the top cap (103) and bottom cap (104) being provided with a corresponding screwthread so that the top cap (103) can be screwed onto the screwthread (105) on the top end and the bottom cap (104) can be screwed onto the screwthread (106) at the bottom end, in a standby position, and so that the bottom cap (104) can be screwed onto the screwthread (105) at the top end after removal of the top cap (103) from the top end and introduction of the biological sample into the flask.

4. A device according to claim 2, characterized in that the flask is provided with a handle (116).

5. A device according to claim 4, characterized in that the flask, the caps and the handle are made from a plastic material.

6. A device according to claim 4, characteristic in that the handle (116) is provided in the center with a large aperture (118).

7. A device according to claim 6, characterized in that the flask, the caps and the handle are made from a plastic material.

8. A device according to claim 4, characterized in that the handle (116) can fit on a hook (113) provided on the flask (100), for which purpose it comprises a transverse slot (117) and a loop (115) which can be fitted against the wall of the flask (100).

9. A device according to claim 8, characterized in that the flask, the caps and the handle are made from a plastic material.

10. A device according to claim 4, characterized in that the wall of the flask (100) is extended downwardly beyond the bottom (102) and constitutes a circular free edge (120) around a bottom cylindrical closure member, the bottom of the flask being lined with a bacteriostatic agent.

11. A device according to claim 10, characterized in that the flask, the caps and the handle are made from a plastic material.

12. A device according to claim 1, characterized in that the flask (100) is cylindrical and is of a circular cross-section.

13. A device according to claim 1, characterized in that the first closure means is an operculum (107).

14. A device intended to facilitate the taking of an excretal biological sample while eliminating the risks of contamination of the biological sample which is thus collected, the device being characterized in that it comprises a flask (100) having an open top end (101) sealingly closed by a first closure means (103, 107), a closed bottom end (102) capped by a bottom cap (104), the bottom cap (104) being intended to fit over the top end (101) after removal of the first closure means (103, 107) and introduction of the biological sample into the flask (100), and a handle (116) attachable to the flask, the handle (114) having a flat tongue (116) provided with a wide, longitudinally extending aperture (118) for preventing drops of the biological sample from reaching the fingers of a person holding the flask.

* * * * *